United States Patent [19]

Berkowitz et al.

[11] 4,416,751

[45] Nov. 22, 1983

[54] PROCESS FOR PRODUCING A FERROFLUID

[75] Inventors: Ami E. Berkowitz; John L. Walter, both of Schenectady, N.Y.

[73] Assignee: General Electric Co., Schenectady, N.Y.

[21] Appl. No.: 305,310

[22] Filed: Sep. 24, 1981

Related U.S. Application Data

[63] Continuation of Ser. No. 133,587, Mar. 24, 1980, abandoned.

[51] Int. Cl.[3] .............................................. C07C 2/80

[52] U.S. Cl. .................................. 204/165; 204/168; 252/62.52; 252/62.54; 252/309; 252/314; 428/900

[58] Field of Search .................. 252/309, 62.54, 62.52; 204/172, 192 M, 165, 168; 427/128; 428/900; 524/440

[56] References Cited

U.S. PATENT DOCUMENTS

| | | | |
|---|---|---|---|
| 2,018,161 | 10/1935 | Weber | 204/172 |
| 3,228,882 | 1/1966 | Harle et al. | 252/62.54 |
| 3,531,413 | 9/1970 | Rosenweig | 252/309 X |
| 3,668,096 | 6/1972 | Cook | 204/165 |
| 3,740,266 | 6/1973 | Akashi et al. | 252/62.54 X |
| 3,916,038 | 10/1975 | Yamaguchi et al. | 252/62.54 X |
| 3,970,687 | 7/1976 | Braun | 560/169 |
| 4,201,827 | 5/1980 | Heitkamp | 428/900 X |

*Primary Examiner*—Richard D. Lovering

*Attorney, Agent, or Firm*—Jane M. Binkowski; James C. Davis, Jr.; James Magee

[57] ABSTRACT

A ferrofluid comprised of composite particles comprised of polymer-enmeshed magnetic metallic particles in indefinite suspension in a carrier fluid is produced by providing a pair of electrodes formed of a composition which will produce the desired magnetic metallic particles, immersing the electrodes in an organic dielectric liquid, applying a pulsed electric potential between the electrodes, adjusting the gap therebetween until there is an electric discharge eroding an electrode producing magnetic metallic particles enmeshed in polymer, recovering the magnetic material from the dielectric liquid and dispersing the magnetic material in a carrier fluid producing ferrofluid.

5 Claims, 1 Drawing Figure

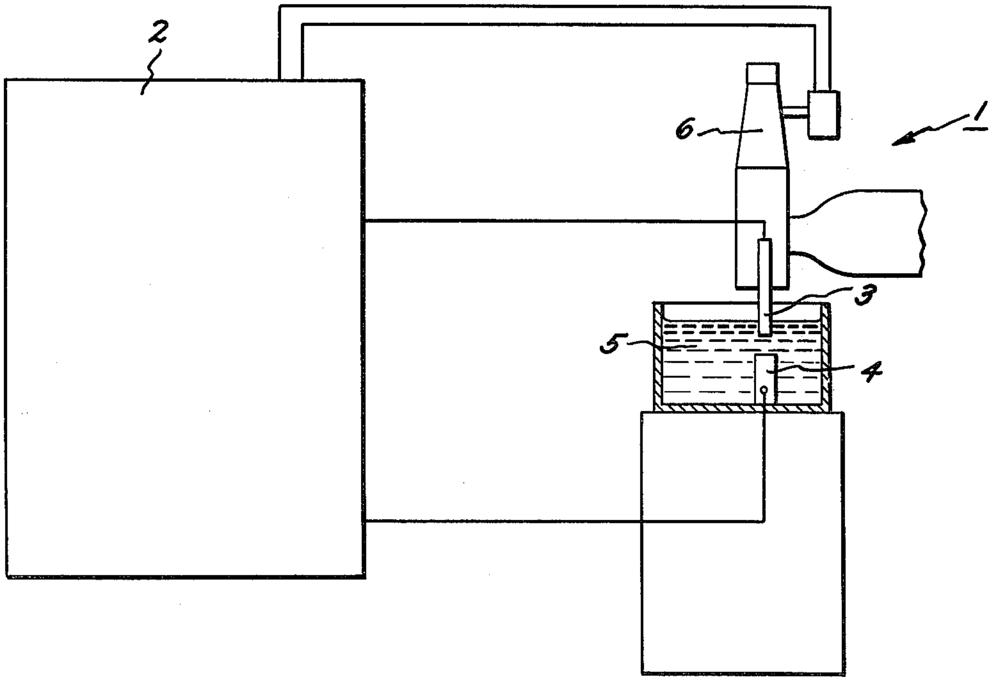
2
6
1
3
5
4

PROCESS FOR PRODUCING A FERROFLUID

This application is a continuation of application Ser. No. 133,587, filed Mar. 24, 1980, and now abandoned.

The present invention relates to a method for making a novel ferrofluid. In one aspect, the present invention relates to a method for making a ferrofluid from magnetic elemental metal or alloy of predetermined composition.

Ferrofluids are liquids in which magnetic particles are suspended. Thus the ferrofluids are responsive to magnetic fields. The response depends on the concentration of magnetic particles and on the specific magnetization of the particles which is determined by their composition and the operating temperatures. Since the effective density of ferrofluids can be selected by an applied field, ferrofluids are being used to separate ores and other materials of different densities. Since their properties are temperature dependent, ferrofluids can be circulated without pumps by local heating and by applying magnetic field gradients. This property has led to current efforts to develop cooling and energy generating systems using ferrofluids. A number of other applications such as magnetic clutches, vacuum seals, pressure seals, display units, etc. are under production or development.

In order for the prior art magnetic particles to remain in suspension in the ferrofluids, they must be very small—typically less than 100 Å diameter and coated with an organic surfactant to prevent agglomeration. At present, ferrofluid particles are all ferrites, mostly magnetite, $Fe_3O_4$. Since ferrites are oxides, this, of course, limits their intrinsic magnetization to a lower value than for most magnetic metals. In addition, ferrofluids are expensive. They are produced by either grinding ferrites in the carrier fluid, with a surfactant for coating, for long times, up to 1000 hours, or by co-precipitating the ferrite particles in an aqueous solution and then coating and transferring them to a non-aqueous solution if required.

The present invention overcomes the disadvantages of the prior art ferrofluids and is effective in the economical production of ferrofluids with high magnetization per unit volume from a wide range of materials.

Briefly stated, the present process comprises providing a pair of electrodes formed of the composition required of the magnetic metallic particles, immersing the electrodes in an organic dielectric liquid, applying a pulsed electric potential between the electrodes and adjusting their gap until there is an electric discharge between the electrodes eroding at least one electrode forming metallic particles in the liquid which become polymer-enmeshed by the polymerization of the dielectric liquid, recovering the magnetic material from the dielectric liquid, dispersing the magnetic material in a carrier fluid and recovering the resulting ferrofluid.

The present ferrofluid is comprised of a carrier fluid having in indefinite suspension therein composite particles comprised of magnetic metallic particles adherently attached to or enmeshed in organic polymer.

Those skilled in the art will gain a further and better understanding of the pesent invention from the detailed description set forth below, considered in conjunction with the accompanying FIGURE forming a part of the specification which is a sectional view through an apparatus for carrying out the present process.

Specifically, the accompanying FIGURE is a schematic of an electric discharge machine 1. Power supply 2 produces high energy current pulses at a high frequency which are required at the gap between the electrodes to produce the electric discharge or spark therebetween which erodes the electrode producing the metallic particles in the organic dielectric liquid 5. Power supply 2 preferably produces current pulses at the rate of 400 to 200,000 per second to attain the desired rate of erosion of one or both of the electrodes. The current pulses can be fed through leads connected to the electrodes 3 and 4 as shown.

In carrying out the present process, negative electrode 3 and positive electrode 4 have the composition required of the metallic particles to be formed. The electrodes are inserted in dielectric liquid 5. By means of hydraulic cylinder 6, electrode 3 is adjusted to produce the gap desired between the electrodes. Specifically, as negative electrode 3 is moved toward positive electrode 4 in the fluid, the electric field between the electrodes increases until there is an electric discharge or spark between the electrodes eroding one or both electrodes producing metallic particles in the liquid which become adherently attached to or enmeshed in organic polymer formed from the dielectric liquid.

The power supply is maintained to charge the electrodes and produce the electric discharge between the electrodes necessary to erode electrode and produce the magnetic metallic particles desired for the ferrofluid. In the present process, the rate of erosion of electrode and the metallic particle size produced by such erosion is determinable empirically, i.e. largely by the total electrical energy (amperage) and/or frequency produced by power supply 2, by the gap or space between the electrodes and the specific composition of the electrodes.

The erosion of electrode in the present process produces at least in a significant or substantial amount metallic particles enmeshed in or attached to organic polymer which in such form are indefinitely suspendible in the carrier fluid used for producing the ferrofluid, and generally, such metallic particles can range up to about 1000 Angstroms in size.

The pair of electrodes used in the present process are of the composition required of the metallic particles to be formed. Specifically, the electrodes are composed of any metallic material which is sufficiently electrically conductive to produce an electric discharge between the electrodes and which is eroded by such electric discharge to produce metallic particles which are magnetic, i.e. which become magnetized when subjected to a magnetizing field.

Representative of such electrode materials is elemental iron, nickel, cobalt and alloys thereof. Additional examples of electrode materials are alloys of FeSi, Fe-B, Fe-Ni-Co, Fe-Ni-Co-Si, Fe-Ni-Co-B, Fe-B-Si and Fe-Co-Si-B.

In the present invention, the metallic particles produced by erosion of electrode have the same composition as that of the electrode. However, in a few instances where the electrode is formed of a significantly reactive elemental metal such as iron or an alloy, a substantial portion of the metallic particles produced are carbides.

The present organic dielectric liquid need only have sufficient dielectric strength for the present erosion of electrode to be carried out and should have no significant deleterious effect on the electrodes or magnetic metallic particles produced. Representative of the dielectric liquids useful in the present invention are aliphatic hydrocarbons, aromatic hydrocarbons, halogenated hydrocarbons, organosiloxanes and mixtures thereof. Typically these include heptane, octane, dodecane, mineral oil, kerosene, carbon tetrachloride, trichloroethylene, benzene, toluene, and polydimethylsiloxane.

In the present process substantially all of the metallic particles formed by erosion of electrode are adherently enmeshed in or attached to polymer. The metallic particles can be completely or partly enmeshed in polymer or otherwise attached to polymer. Generally, the polymer is in a fibrous or filamentary form. It is believed that the polymer may form by phenomena such as reaction of the dielectric liquid to the electric discharge and/or reaction to the hot metallic particles produced by erosion of electrode. The particular amount of polymer formed can vary depending largely on the nature of the dielectric liquid as well as the strength of electric discharge and the volume and nature of the metallic particles produced.

When electric discharging is stopped, solid matter is left in the dielectric liquid which is comprised of the present composite particles useful in forming ferrofluid as well as excess polymer and larger sized metallic particles not useful for forming ferrofluid. If left standing, the solid matter settles to the bottom depositing from the dielectric liquid by gravity with the present composite particles being pulled down by the heavier surrounding solid matter.

A number of techniques can be used to separate the magnetic portion of the solid matter from the non-magnetic debris such as excess polymer. Preferably, the solid matter is subjected to a magnetizing field to recover the magnetic portion therefrom. For example, a magnet can be immersed in the dielectric liquid and solid matter therein to collect and recover the magnetic material.

The recovered magnetic material is comprised of the present composite particles and larger sized metallic particles not useful in forming ferrofluid. This magnetic material is then mixed with the desired carrier fluid to produce the present ferrofluid. Such mixing can be carried out by a number of techniques, and preferably, it is carried out ultrasonically to thoroughly disperse the magnetic matter in the fluid. The resulting mixture can be left standing so that heavier matter can deposit out settling to the bottom leaving the present polymer-enmeshed or attached metal particles in indefinite suspension in the fluid. The resulting ferrofluid can then be recovered by techniques such as decantation. To improve yield, the procedure can be repeated with the deposited solid matter being dispersed in additional carrier fluid to separate any remaining present composite particles therefrom leaving them in indefinite suspension in the carrier fluid.

The carrier fluid used in producing the present ferrofluid should have no significant deleterious effect on the metallic particles. Specifically, the particular carrier fluid used depends largely on the final application of the ferrofluid. Representative of the carrier fluids are organic fluids such as benzene, light oils such as dodecane, dielectric fluids such as kerosene and silicone oil, and aqueous fluids such as, for example, water.

A number of conventional techniques can be used to produce the present ferrofluid having the desired concentration and magnetic properties. For example, the initial amount of carrier fluid used in producing ferrofluid can be controlled, or carrier fluid can be evaporated or added to the ferrofluid. In addition, ferrofluids of various concentrations can be admixed to produce the desired ferrofluid.

The ferrofluid of the present invention is comprised of carrier fluid having in indefinite suspension therein composite particles comprised of magnetic metallic particles adherently enmeshed in or attached to polymer. By indefinite suspension it is meant herein a stable suspension at room temperature, i.e. the present composite particles remain in suspension without depositing from the carrier fluid under gravity. The composite particles of the present ferrofluid are of a size and density which maintains them in indefinite suspension in the particular carrier fluid. Ordinarily, the polymer component of the composite particle imparts to it a density significantly lower than that of the component metallic particle thereby maintaining or helping to maintain the metallic particle in indefinite suspension in the carrier fluid. The metallic particles, themselves, range in size up to about 1000 Angstroms, and preferably from about 25 Angstroms to about 100 Angstroms. As used herein, a magnetic metallic particle is a particle which is magnetically responsive, i.e. it becomes magnetized when subjected to a magnetizing field.

The present ferrofluid is magnetically responsive and its particular composition and concentration depend on its final application. Specifically, its magnetic response depends on the concentration of magnetic metallic particles therein and on the specific magnetization of the particles which is determined by their composition and operating temperatures. The volume of composite particles in indefinite suspension in the carrier fluid is at least sufficient to make the resulting suspension, i.e. ferrofluid, magnetically responsive. For a majority of applications, the volume fraction of magnetic composite particles in indefinite suspension in the present ferrofluid ranges from about 1% to about 10% by volume of the ferrofluid, and from about 10% by volume to about 50% by volume of the total volume of the indefinitely suspended composite particles is metallic material.

In the present invention, the specific composition and characteristics of the organic polymer enmeshing or attached to the magnetic metallic particles depends largely on the dielectric liquid from which it is formed as well as the specific conditions under which it is produced, such as the nature of the electric discharge. The polymer is highly adherent to the metallic particles generally forming polymeric fibers therebetween producing small rafts or membranes of the present composite particles in indefinite suspension in the fluid.

The particular volume of polymer in the ferrofluid can vary widely provided it has no significant deleterious effect on its magnetic properties.

The present process is useful for producing ferrofluids which can range widely in composition and magnetic properties. Generally, for most applications, the magnetization of the present ferrofluid range from about 100 gauss to about 500 gauss. The present ferrofluid is useful in separating ores and other materials of different densities.

For purposes of examination, the present composite particles were recovered from indefinite suspension in the ferrofluid by magnetic methods. The wet recovered composite material was somewhat gummy, and after being dried it was fairly hard. Attempts to separate the metallic particles from the polymer in the wet and dried states were unsuccessful.

The invention is further illustrated by the following examples:

EXAMPLE 1

$Fe_{75}Si_{15}B_{10}$ electrodes were fabricated from castings prepared by melting, in an induction furnace under an argon atmosphere, 99.91% Fe, 99.8% B and Si with 1 ppb impurities. The melt was cast under argon into a copper chill mold, producing a casting 1.25 cm thick, 7.6 cm wide, and 12.7 cm long. A 3 cm diameter cylinder electrode was cut from the casting by electric discharge machining. A flat piece of the casting with a straight edge was used for the other electrode.

The dielectric liquid was held in a 20 cm. diameter brass container which was mounted on the bed of a commercially available electric discharge machine. The container was slowly moved back and forth by the bed. The electrode with a straight edge was mounted to the bottom of the container and moved with it. The cylindrical electrode was mounted above it to the rotating spindle of the electric discharge machine and was rotated during electric discharging. A pulsed electric potential was supplied to the electrodes from a power supply. The gap between the two electrodes was automatically adjusted to insure optimum discharge conditions, i.e. it was controlled to keep it just at the point that it was discharging. An array of permanent magnets within a thin walled aluminum cylinder was placed at the bottom of the brass container to collect magnetic particles.

The dielectric liquid placed in the container was kerosene. With the electrodes immersed in the kerosene, power was supplied to give a pulse frequency of 10 kHz, a current of 1.5 amperes and a capacitance of 4.5 mfd. Electric discharging between the electrodes was maintained for about 6 hours.

At the end of this time the power was shut off and the permanent magnet was removed. The magnetic particles adhering to the magnet were released by removing the magnets from within the aluminum cylinder, and they were washed three times in methylene chloride with ultrasonic agitation to displace the kerosene and to remove as much as possible of the polymeric material. Between each washing the particles were collected magnetically.

The resulting magnetic material was dispersed finally in 1000 ml of methylene chloride with ultrasonic agitation to produce a thorough dispersion and then left to stand at room temperature for three days. During this time, a portion of the magnetic material deposited out of the dispersion leaving a portion of the magnetic material in indefinite suspension. The suspension was separated from the deposited material by decantation.

The suspension was concentrated by evaporating the methylene chloride until a magnetically responsive ferrofluid was produced at room temperature. The solid matter appeared to be uniformly distributed in the ferrofluid. In 2 cc of the ferrofluid there were 23 mg of solid matter in indefinite suspension, i.e. the ferrofluid had about 0.6% by volume of solid matter in indefinite suspension. The solid matter was comprised of composite particles composed of magnetic metallic particles enmeshed in or attached to polymeric material. About 80% by volume of the solid matter, i.e. composite particles, was polymer and about 20% by volume was metallic particles. The composite particles were in the form of small filamentary rafts or membranes.

At room temperature the ferrofluid was highly magnetically responsive to a magnetic field of approximately 100 oersteds, i.e. the ferrofluid moved in response to the magnetic field. It had a magnetization of 110 gauss.

The composite particles in indefinite suspension in the ferrofluid were collected magnetically and examined. The wet material, which was gummy, was dried under nitrogen at room temperature.

The dried composite particles were relatively hard. Their magnetization, which was measured in a vibrating sample magnetometer, was 15.3 emu per gram.

Portions of the dry composite particles were subjected to X-ray analysis, optical, scanning electron and transmission electron microscopy. The metallic particles contained various magnetic phases of Fe, Si and B which corresponded to the composition of the electrodes.

The metallic particles, themselves, ranged in size from about 10 Angstroms to about 500 Angstroms and mostly from about 25 Angstroms to about 50 Angstroms. The polymer component was determined to be polymeric organic matter, and the metallic particles appeared to be uniformly distributed in the polymer.

The polymer was highly adherent to the metallic particles in both the wet and dried states. Samples of the composite material were immersed in acetone and xylene. Other samples were treated for weeks in an Soxhet extractor with tetralene. Still other samples were etched with plasma or treated with ozone. None of these treatments showed any significant deterioration in the adherence or the bond between the polymer and metallic particles, or any significant reduction in the concentration of the polymeric material.

EXAMPLE 2

A number of runs were made with the same $Fe_{75}Si_{15}B_{10}$(at.%) electrodes of Example 1 using the same apparatus in order to determine the influence of operating parameters on particle properties and yield. A typical run was about 6 hours. The dielectric liquids were dodecane and silicone oil, as well as kerosene. The ranges of the principle operating parameters were: pulse frequency, 10–40 kHz; current, 1.5–5.0 amperes; capacitors, 4.5–18 mfd.

The procedures for recovering the magnetic material and for preparing the suspensions were the same as that disclosed in Example 1. Specifically, the resulting washed magnetic material was dispersed finally in 1000 ml of methylene chloride with ultrasonic agitation to produce a thorough dispersion and then left to stand at room temperature for three days. During this time, a portion of the magnetic material sedimented out of the dispersion leaving a portion of the magnetic material in indefinite suspension, and the suspension was separated from the sedimented material by decantation.

The composite particles in indefinite suspension in each suspension were collected magnetically and examined. The wet material, which was gummy, was dried under nitrogen at room temperature. The dried composite particles were relatively hard. Their magnetization per gram was measured in the same manner as in Example 1 and found to be approximately the same as that of Example 1.

It is obvious that had these suspensions been concentrated by evaporating methylene chloride therefrom, magnetically responsive ferrofluids would have been produced.

EXAMPLE 3

The procedure used in this example was the same as that disclosed in Example 2 except that the electrodes were $Fe_{87.2}B_{17.3}$(at.%).

The composite particles had a magnetization per gram which was approximately the same as that disclosed in Example 1.

It is obvious that had this suspension been concentrated by evaporating methylene chloride therefrom, a magnetically responsive ferrofluid would have been produced.

What is claimed is:

1. A process for producing a ferrofluid consisting essentially of composite particles composed of polymer-attached magnetic metallic particles in indefinite suspension in a carrier fluid which consists essentially of providing a pair of electrodes, immersing the electrodes in an organic dielectric liquid, applying a pulsed electric potential between the electrodes, adjusting the gap therebetween until there is an electric discharge eroding an electrode producing particulate magnetic material containing said composite particles composed of magnetic metallic particles adherently attached to organic polymer formed by the polymerization of said dielectric liquid, said polymer being in a fibrous or filamentary form, said electrodes being formed of a metallic composition which produces said magnetic metallic particles by said erosion, recovering said magnetic material from the dielectric liquid, and dispersing said recovered material in a carrier fluid in which said composite particles become indefinitely suspended, said composite particles being in the form of filamentary rafts or membranes of a size and density which maintains them in indefinite suspension in said carrier fluid.

2. A process according to claim 1 wherein said metallic particle is an elemental metal.

3. A process according to claim 1 wherein said metallic particle is a metal carbide.

4. A process according to claim 1 wherein said metallic particle is an alloy.

5. A process according to claim 1 wherein said composite particles range in volume from about 1% to about 10% by volume of said ferrofluid.

* * * * *